(12) United States Patent
Aslami

(10) Patent No.: US 6,587,805 B2
(45) Date of Patent: Jul. 1, 2003

(54) TESTING A WRITE TRANSDUCER AS A READER

(75) Inventor: Mohammad Shoaib Aslami, Loveland, CO (US)

(73) Assignee: Seagate Technology LLC, Scotts Valley, CA (US)

(*) Notice: Subject to any disclaimer, the term of this patent is extended or adjusted under 35 U.S.C. 154(b) by 19 days.

(21) Appl. No.: 09/790,846

(22) Filed: Feb. 20, 2001

(65) Prior Publication Data
US 2001/0037183 A1 Nov. 1, 2001

Related U.S. Application Data
(60) Provisional application No. 60/184,934, filed on Feb. 25, 2000.

(51) Int. Cl.$^7$ .......................... G01L 25/00; G01M 10/00
(52) U.S. Cl. ...................................................... 702/115
(58) Field of Search ............................... 702/115, 117, 702/108; 324/210, 228; 360/313–318

(56) References Cited

U.S. PATENT DOCUMENTS

| | | | |
|---|---|---|---|
| 3,699,430 A | | 10/1972 | Kruklitis |
| 3,710,235 A | | 1/1973 | Barrager et al. |
| 5,465,186 A | | 11/1995 | Bajorek et al. |
| 5,491,597 A | | 2/1996 | Bennin et al. |
| 5,514,953 A | | 5/1996 | Schultz et al. |
| 5,555,619 A | * | 9/1996 | Maggio et al. ............... 29/860 |
| 5,589,771 A | | 12/1996 | Chur |
| 5,589,777 A | * | 12/1996 | Davis et al. ................. 324/537 |
| 5,691,857 A | * | 11/1997 | Fitzpatrick et al. ...... 360/77.06 |
| 5,703,485 A | | 12/1997 | Guo et al. |
| 5,721,488 A | | 2/1998 | Sakai et al. |
| 5,754,369 A | * | 5/1998 | Balakrishnan ........... 360/264.2 |
| 5,754,370 A | | 5/1998 | Tsuchiya et al. |
| 5,821,746 A | * | 10/1998 | Shelor ........................ 324/210 |
| 5,841,318 A | | 11/1998 | Cram |
| 5,844,754 A | * | 12/1998 | Stefansky et al. ........ 360/266.1 |
| 5,898,303 A | * | 4/1999 | Umanskiy et al. .......... 324/210 |
| 5,982,173 A | * | 11/1999 | Hagen ........................ 324/212 |
| 5,982,568 A | * | 11/1999 | Yamamoto .................... 360/31 |
| 6,025,712 A | * | 2/2000 | Mian .......................... 324/210 |
| 6,025,988 A | * | 2/2000 | Yan ............................ 361/682 |
| 6,111,406 A | * | 8/2000 | Garfunkel et al. .......... 324/210 |
| 6,118,602 A | * | 9/2000 | de la Soujeole ............... 360/48 |
| 6,172,832 B1 | * | 1/2001 | Dovek et al. ................. 360/66 |
| 6,271,978 B1 | * | 8/2001 | Block et al. .................. 360/46 |
| 6,310,740 B1 | * | 10/2001 | Dunbar et al. ................ 360/46 |
| 6,340,885 B1 | * | 1/2002 | Hachisuka et al. ......... 324/210 |
| 6,346,809 B1 | * | 2/2002 | Karam, II .................... 324/210 |
| 6,400,526 B2 | * | 6/2002 | Crue, Jr. et al. ............ 360/126 |
| 6,411,452 B1 | * | 6/2002 | Cloke ........................... 360/51 |
| 2001/0055174 A1 | * | 12/2001 | Teterud ........................ 360/68 |

* cited by examiner

Primary Examiner—John Barlow
Assistant Examiner—Demetrius R. Pretlow
(74) Attorney, Agent, or Firm—Merchant & Gould P.C.

(57) ABSTRACT

A system for testing inductive write head elements of a head stack assembly ("HSA"). A completed HSA is placed in a test apparatus. Test probes are aligned and placed in electrical contact with the head elements, preferably at a location between the head and the preamplifier. The HSA is then placed in a changing magnetic field. A low frequency magnetic field may be applied to test the head elements. The changing magnetic field induces electrical signals within the head elements. By analyzing these electrical signals, the condition and characteristics of the each head element can be determined.

15 Claims, 5 Drawing Sheets

TESTING A WRITE TRANSDUCER AS A READER

Related Applications

This application claims priority of U.S. provisional application Serial No. 60/184,934, filed Feb. 25, 2000.

FIELD OF THE INVENTION

This application relates generally to testing systems for magnetic media storage devices and more particularly to testing read/write head elements prior to final assembly of the storage device.

BACKGROUND OF THE INVENTION

The need for more efficient data storage devices has become critical with the staggering pace of advances in computer technology. The most common data storage device used today is the disc drive. Most disc drives are composed of one or more magnetic media discs attached to a spindle. A spindle motor rotates the spindle and discs at a constant high speed. An actuator assembly adjacent to the disc(s) has actuator arms extending over the discs, each with one or more flexures extending from each actuator arm. A read/write head is mounted at the distal end of each of the flexures. The read/write head includes an air bearing slider enabling the head to fly in close proximity above the corresponding surface of the associated disc. Information is stored on and retrieved from the magnetic media discs via the read/write head.

A flex assembly provides the requisite electrical connection paths for the actuator assembly while allowing pivotal movement of the actuator assembly during operation. The flex assembly includes circuitry to which head wires are connected; the head wires being routed along the actuator arms and the flexures to the heads. The flex assembly typically includes circuitry for controlling the write currents applied to the heads during a write operation and a preamplifier for amplifying read signals generated by the heads during a read operation. The flex assembly terminates at a flex bracket for communication through the base deck to a disc drive printed circuit board mounted to the bottom side of the disc drive. The actuator assembly and the flex assembly are usually combined before the disc drive is assembled. The product of this combination is called the head stack assembly ("HSA").

Disc drive manufacturers are attempting to increase the amount of information stored on existing disc drives to meet the increased demand for information storage. Manufacturers have, for example, increased the areal density of their disc drives to fit more information on a constant sized disc. Areal density is a measurement of the number of bits of information that can be stored on one square inch of disc space. Increased areal density, however, requires a sophisticated read/write head to access information stored on the disc media. Some current disc drives use a dual element transducer head to overcome some of the problems encountered with increased areal density. One element is used to read data and a second element is used to write data in a dual element transducer head. Some disc drives utilize a "mixed" technology head design. In a mixed technology head, the read element transducer is of the magnetoresistive (MR) type, whereas the write element transducer is of the inductive type.

A HSA, as mentioned above, usually consists of heads, flexures, actuator arms, head wires, and a flex assembly with a preamplifier. Many processing steps are required to manufacture a HSA. The likelihood that the delicate read/write heads will be damaged increases as each processing step is completed. Electrostatic discharge or physical contact between the head and some other mechanical part, for example, may damage the sensitive read/write elements of the head. As a result of this damage risk, a manufacturer must verify that the read/write heads operate properly before placing the HSA into a disc drive. Current verification methods, however, are time consuming, expensive, and subject the heads to an additional risk of damage.

Dynamic electrical testing is the most common method of testing mixed technology heads. The HSA is placed in a dynamic electrical tester ("DET"). A DET simulates actual disc drive operation by placing the HSA within a magnetic media cylinder and then spinning the magnetic media cylinder at high speed. The magnetic media cylinder is basically a stack of one or more discs that imitates the disc, or discs, in a disc drive. A signal, sent by the DET through the HSA's inductive write head element, is stored on the magnetic media cylinder. Next, the DET uses the HSA's MR read head element to retrieve the data written by the inductive write element. A determination of whether the head elements are functioning properly can be made by comparing these two signals. Although very accurate, dynamic electrical testing is time consuming, expensive, and potentially destructive (the heads can be destroyed if they come in contact with the media being spun at high speeds).

Another method of testing a HSA is called static testing. In static testing, the HSA is placed within a changing magnetic field; the variation of the magnetic field induces small signals within the head elements. These signals are then sent through the preamplifier. A signal analyzer connected at the output of the preamplifier reads the signals. Static testing, although faster, cheaper, less complicated, and less destructive than dynamic testing, has its own inherent limitations.

Current static testing methods, for example, do not allow for amplitude or resistance testing of the write head. The only tests currently available for the write head during static testing are those provided by the preamplifier vendor, such as a write unsafe ("WUS") or a fault ("FLT") test among others. The outputs of the preamplifier are monitored when using current static testing methods. A logic high on the FLT pin, for example, may indicate that a low write data signal exists at the write head, the write head is shorted to ground, the write head was illegally selected, the write head is an open circuit, or low DC power is present at the preamplifier among others. Current static testing does not allow the write head amplitude signal to be analyzed, instead, dynamic testing must be used to analyze this signal.

The need to design a "receiver" for the write element is a second limitation of static testing. The write signal, using current static testing methods, must be "written" to something in order to test the write head. The magnetic media cylinder is used in dynamic testing, however, such a magnetic media is not used in static testing. Instead, a receiver is used. The receiver is designed to mimic the characteristics of the magnetic media. The write signal is analyzed at the receiver to determine the characteristics of the write element. A large amount of money and time must be invested to design the receiver and its supporting circuitry for current static testing methods. It is in respect to these considerations and others that the present invention has been made.

SUMMARY OF THE INVENTION

In accordance with the present invention, the above and other problems are solved by a testing system that does not require dynamic testing and permits the use of a low frequency magnetic field to test the inductive write head elements. In a preferred embodiment of the present invention, the completed head stack assembly ("HSA") is placed in the test apparatus. Test probes are aligned and placed in electrical contact with the electrical leads coming from each head element, between the head elements and the preamplifier. The HSA is then placed in a changing magnetic field. The changing magnetic field induces electrical signals within the inductive write head element. The condition and characteristics of the inductive write head element can be determined by analyzing the induced electrical signals.

In accordance with other aspects, the present invention relates to a method of testing an inductive write head element in an assembled HSA by placing test probes in electrical contact with the electrical connections of the inductive head element, between the inductive head element and the preamplifier, generating a changing magnetic field around a portion of the inductive write head element, inducing a test signal within the inductive write element, and analyzing the test signal induced in the inductive write element and determining whether the inductive write element is functioning properly.

Furthermore, the present invention eliminates the problems associated with static testing. Testing an inductive write head as a reader, for example, allows the same low frequency magnetic field that is generated to test the read head to be used for testing the inductive write head. The amplitude of the signal induced in the inductive write head and the resistance of the inductive write head can be measured directly, before the signals enter the preamplifier. The testing limitations imposed by the preamplifier vendors are therefore eliminated without resorting to dynamic testing.

Additionally, the present invention eliminates the need to design a receiver for testing the inductive write head. The same low frequency signal that is used to test the read element is used to test the inductive write element. The need to write a signal to the magnetic media, or to a receiver that mimics the magnetic media, is therefore eliminated. The large investment of money and time need to design the receiver and supporting circuitry is also eliminated.

These and various other features as well as advantages which characterize the present invention will be apparent from a reading of the following detailed description and a review of the associated drawings.

DETAILED DESCRIPTION

Figure 1:
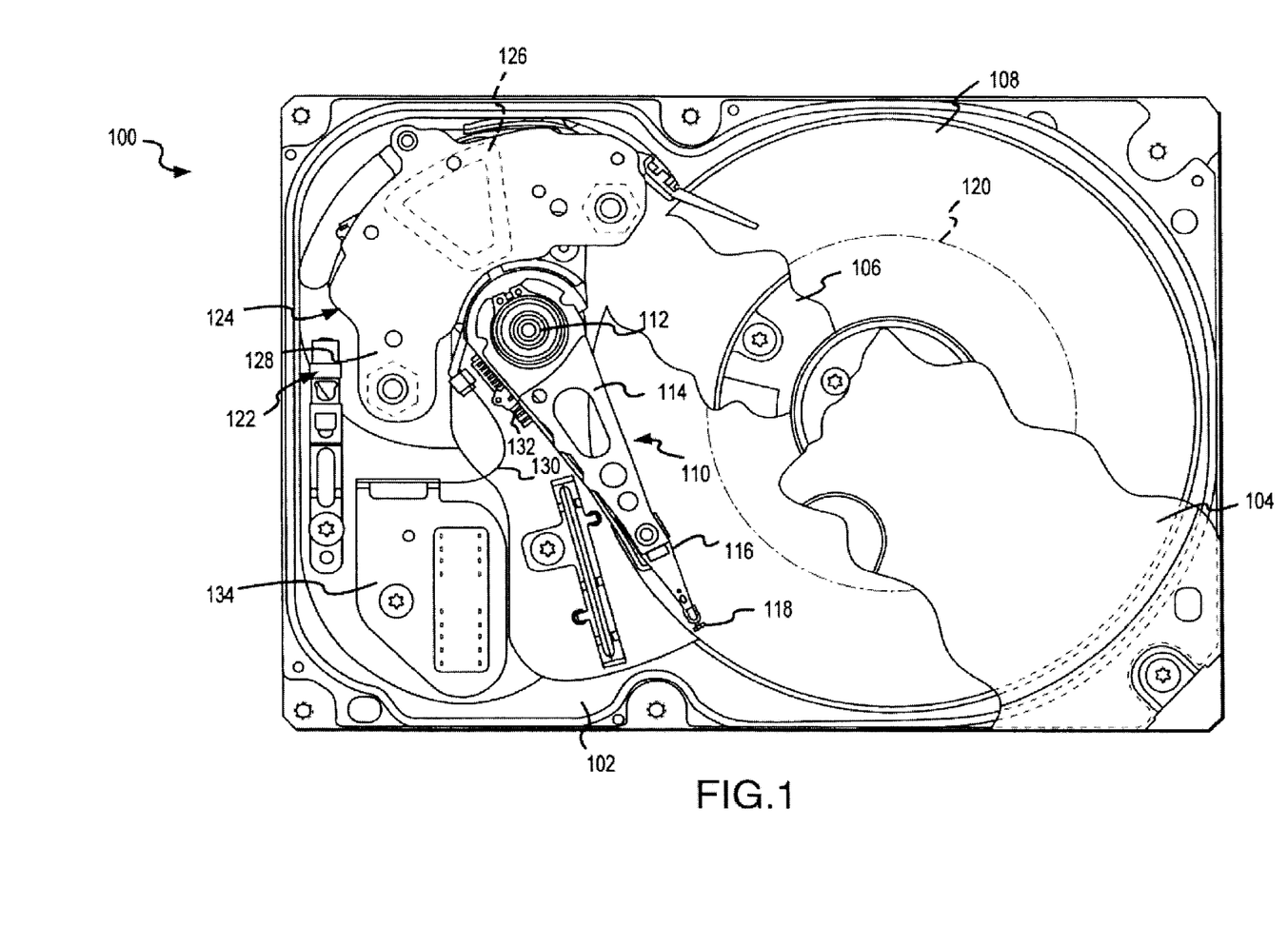
FIG. 1 is a plan view of a disc drive showing the primary internal components, including a head stack assembly.

A disc drive 100 constructed in accordance with a preferred embodiment of the present invention is shown in FIG. 1. The disc drive 100 includes a base 102 to which various components of the disc drive 100 are mounted. A top cover 104, shown partially cut away, cooperates with the base 102 to form an internal, sealed environment for the disc drive in a conventional manner. The components include a spindle motor 106 which rotates one or more discs 108 at a constant high speed. Information is written to and read from tracks 120 on the discs 108 through the use of an actuator assembly 110, which rotates during a seek operation about a bearing shaft assembly 112 positioned adjacent the discs 108. The actuator assembly 110 includes a plurality of actuator arms 114 which extend towards the discs 108, with one or more flexures 116 extending from each of the actuator arms 114. Mounted at the distal end of each of the flexures 116 is a head 118 which includes an air bearing slider enabling the head 118 to fly in close proximity above the corresponding surface of the associated disc 108.

During a seek operation, the track 120 position of the heads 118 is controlled through the use of a voice coil motor (VCM) 124, which typically includes a coil 126 attached to the actuator assembly 110, as well as one or more permanent magnets 128 which establish a magnetic field in which the coil 126 is immersed. The controlled application of current to the coil 126 causes magnetic interaction between the permanent magnets 128 and the coil 126 so that the coil 126 moves in accordance with the well-known Lorentz relationship. As the coil 126 moves, the actuator assembly 110 pivots about the bearing shaft assembly 112, and the heads 118 are caused to move across the surfaces of the discs 108.

The spindle motor 106 is typically de-energized when the disc drive 100 is not in use for extended periods of time. The heads 118 are moved over park zones near the inner diameter of the discs 108 when the drive motor is de-energized. The heads 118 are secured over the park zones through the use of an actuator latch arrangement 122, which prevents inadvertent rotation of the actuator assembly 110 when the heads are parked.

A flex assembly 130 provides the requisite electrical connection paths for the actuator assembly 110 while allowing pivotal movement of the actuator assembly 110 during operation. The flex assembly includes a preamplifier 132 to which head wires (not shown) are connected; the head wires being routed along the actuator arms 114 and the flexures 116 to the heads 118. The preamplifier 132 typically includes circuitry for amplifying read signals generated by the heads 118 during a read operation. The flex assembly terminates at a flex bracket 134 for communication through the base deck 102 to a disc drive printed circuit board (not shown) mounted to the bottom side of the disc drive 100.

Figure 2:
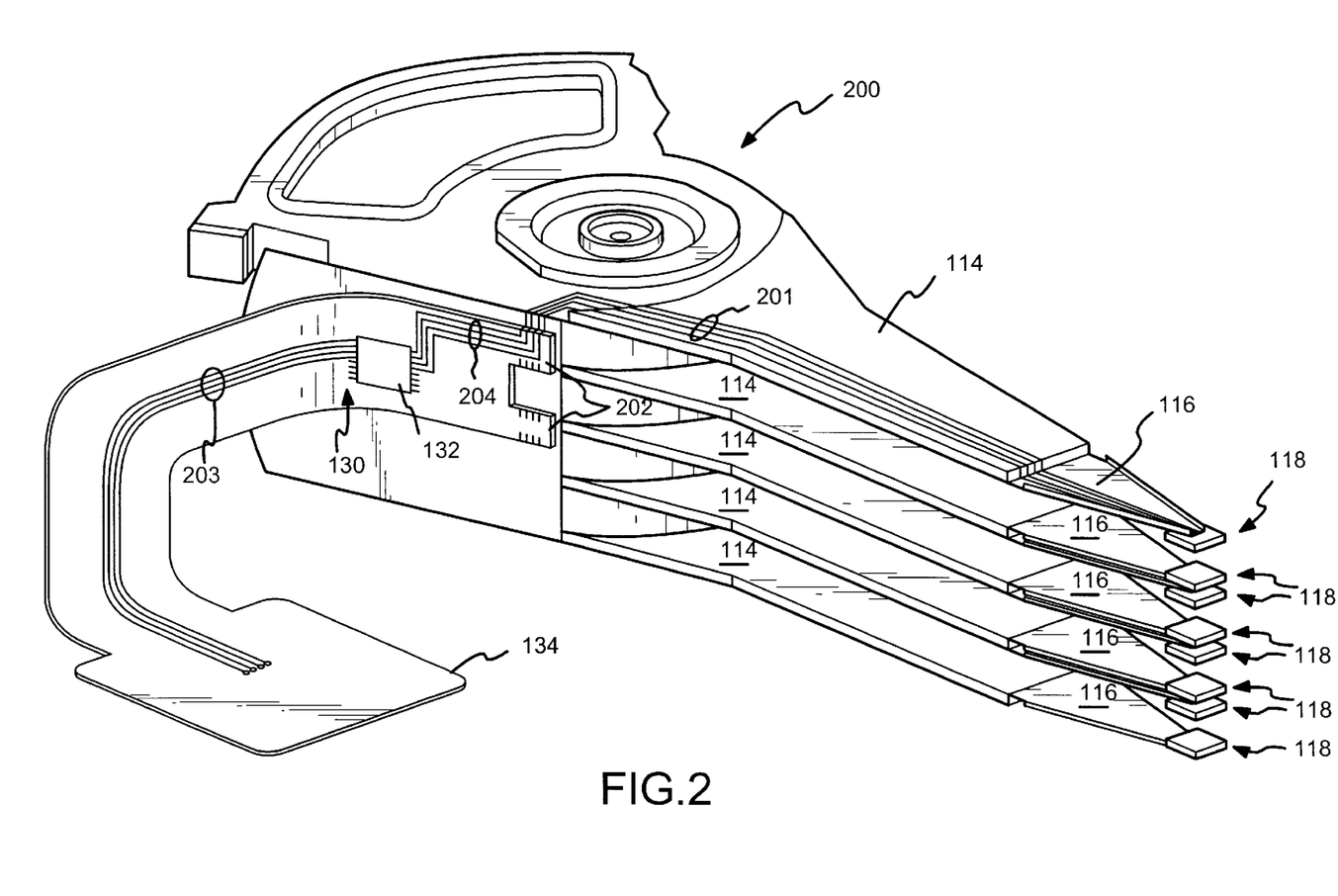
FIG. 2 is a detailed view of head stack assembly in accordance with a preferred embodiment of the present invention.
Figure 3:
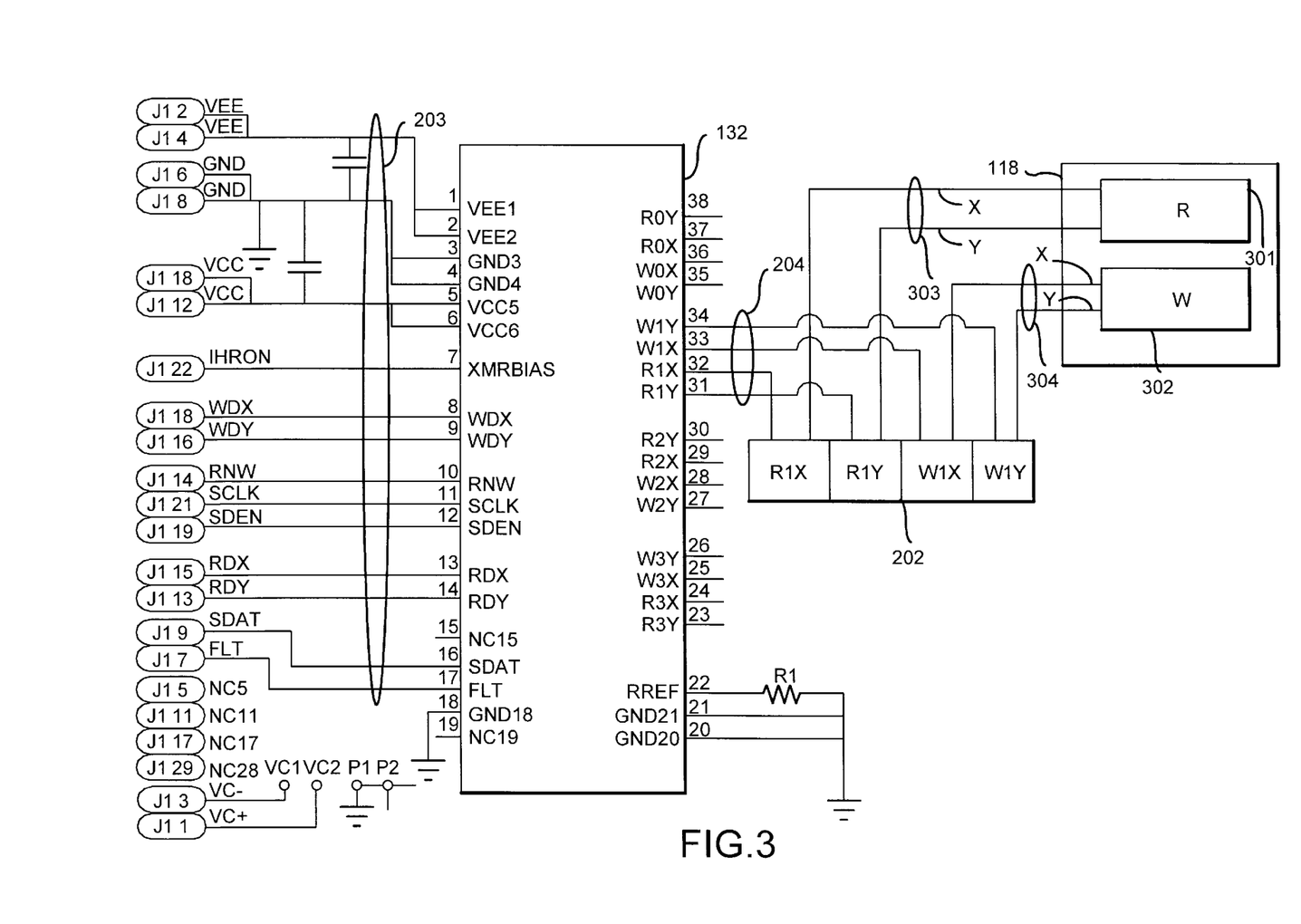
FIG. 3 is a schematic view of a head stack assembly preamplifier and its associated wiring in accordance with a preferred embodiment of the present invention.

The head stack assembly ("HSA") 200, as shown in FIG. 2, includes a plurality of actuator arms 114 with one or more flexures 116 extending from each of the actuator arms 114. Mounted at the distal end of each of the flexures 116 is a read/write head 118. Each read/write head has two elements (as shown in FIG. 3), the read element 301 and the write element 302. Each read/write element 301, 302 is electrically connected to a preamplifier 132 that is integrated into the flex assembly 130. For simplicity, FIG. 2 shows the connections for one read element 301 and one write element 302. Head element electrical leads 201 are electrically connected to the head's 118 elements, run along flexures 116 and actuator arms 114, and terminate at contact pads 202 of flex assembly 130. Contact pads 202 are electrically connected to preamplifier 132 via the preamplifier's 132 gull-wing leads 204. Preamplifier output leads 203 run along flex circuit 130 to flex bracket 134. Flex bracket 134 communicates with the disc drive circuit board (not shown) mounted to the bottom side of the disc drive.

FIG. 3 shows a detailed view of preamplifier 132 electrically connected to read element 301 and write element 302 of read/write head 118 via contact pad 202. Contact pad 202 contains terminations R1X and R1Y for read element electrical leads 303 and terminations W1X and W1Y for write element electrical leads 304 of read/write head 118. The total number of read/write heads 118 connected to preamplifier 132 may vary depending on the application involved. Preamplifier inputs PINS 31–34 are electrically connected to their corresponding contact pad 202 terminations (R1X, R1Y, etc.) via gull-wing leads 204. Electrical connections are made such that read element lead X 303 of read/write head 118 is electrically connected to its corresponding contact pad 202 termination R1X and a gull wing lead 204 electrically connects contact pad 202 termination R1X to preamplifier input PIN 32. Likewise, read element lead Y 303 of read/write head 118 is electrically connected to its corresponding contact pad 202 termination R1Y and a gull wing lead 204 electrically connects contact pad 202 termination R1Y to preamplifier input PIN 31. Electrical connections are also made such that write element lead X 304 of read/write head 118 is electrically connected to its corresponding contact pad 202 termination W1X and a gull wing lead 204 electrically connects contact pad 202 termination W1X to preamplifier input PIN 33. Likewise, write element lead Y 304 of read/write head 118 is electrically connected to its corresponding contact pad 202 termination W1Y and a gull wing lead 204 electrically connects contact pad 202 termination W1Y to preamplifier input PIN 34. This pattern may be repeated for the each read/write head 118 in HSA 200. Preamplifier 132 can support inputs from a multitude of read/write heads 118. Preamplifier outputs PINS 1–19 are electrically connected to the disc drive circuit board (not shown) via output wires 203.

Referring to FIG. 3, the test probes for prior art testing methods (i.e., dynamic and static testing) are placed on the outputs PINS 1–19 or on output leads 203 of preamplifier 132. Test probes, for example, are placed on the RDX position PIN 13 and RDY position PIN 14 to test read element 301 of a selected head 118. Likewise, test probes are placed at the WDX position PIN 8 and WDY position PIN 9 to test write element 302 of a selected head 118. The specific head 118 to be tested in a multiple-head HSA 200 is selected by the technician running the test. A low frequency magnetic field is not used in the prior art testing method to induce a test signal in the head elements because most preamplifiers 132 are not designed to amplify low frequencies signals.

The only tests currently available for the write element 302 during static testing are those provided by the preamplifier vendor, such as a write unsafe ("WUS") or a fault ("FLT") test among others. The outputs of the preamplifier 132 are monitored when using current static testing methods. A logic high on the FLT pin, for example, may indicate that a low write data signal exists at the write element 302, the write element 302 is shorted to ground, the write element 302 was illegally selected, the write element 302 is an open circuit, or low DC power is present at the preamplifier 132 among others. Current static testing does not allow the write element 302 amplitude signal to be analyzed, instead, dynamic testing must be used to analyze this signal. The need to design a "receiver" for the write element 302 is a second limitation of static testing. The write signal, using current static testing methods, must be "written" to something in order to test the write element 302 head. The magnetic media cylinder is used in dynamic testing, however, such a magnetic media is not used in static testing.

Instead, a receiver is used. The receiver is designed to mimic the characteristics of the magnetic media. The write signal is analyzed at the receiver to determine the characteristics of the write element 302. A large amount of money and time must be invested to design the receiver and its supporting circuitry for current static testing methods.

Most preamplifiers 132 would require the addition of a low frequency channel to be able to use a low frequency test signal. Such addition increases the cost of the chip to an undesirable level. As a consequence, under the prior art testing method, a high frequency magnetic field is used to induce test signals in the head elements 301, 302. The high frequency test signals pass-through preamplifier 132 and are measured at preamplifier outputs 203. The high frequency magnetic field, however, also induces undesirable stray signals in the read head element lead wires 303, the write head element lead wires 304, and gull wing leads 204. These stray signals saturate and mask the test signal, rendering high frequency static testing unsatisfactory.

Overcoming the limitations of the prior art static testing required the use of dynamic testing prior to the present invention. In dynamic testing, the test probes are again placed on the outputs PINS 1–19 or output leads 203 of preamplifier 132. HSA 200 is then placed in a dynamic electrical tester ("DET"). The DET has a rotating magnetic media cylinder that simulates the discs in a disc drive 100. A signal is written to the magnetic media using HSA's 200 inductive write elements 302 once the DET's magnetic media cylinder achieves the desired rotational speed. Next, the HSA's 200 read elements 301 are used to read the signal just written. The two signals are compared to determine whether read element 301 and write element 302 are functioning properly. Although accurate, dynamic testing is time consuming and costly. Additionally, the head elements 301, 302 are subjected to the risk of being damaged due to possible contact with the rotating magnetic media.

Figure 4:
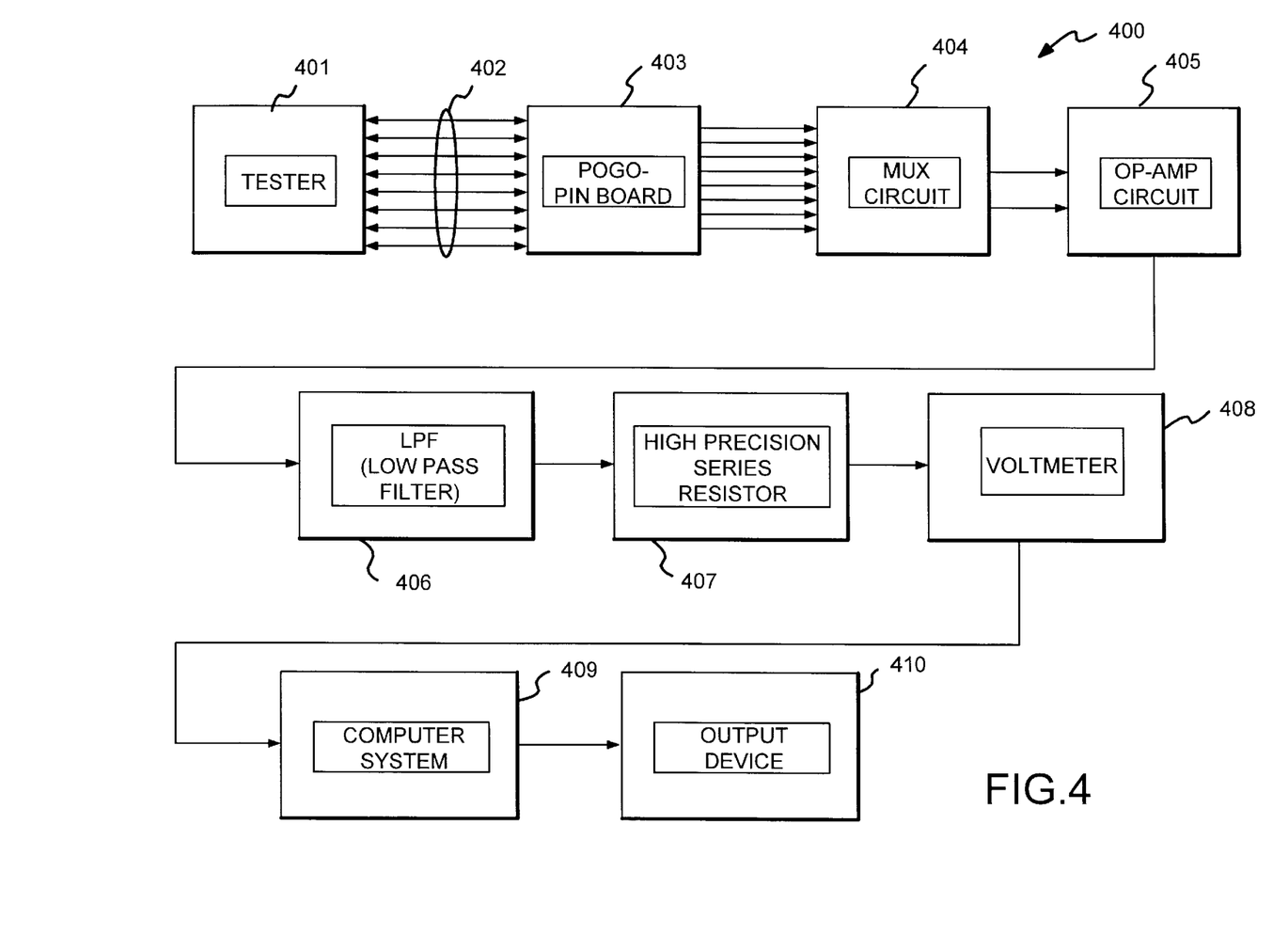
FIG. 4 is a system diagram of a head stack assembly test system in accordance with a preferred embodiment of the present invention.

In an embodiment of the present invention, test probes 402 (as shown in FIG. 4) are located at some point between head 118 and inputs PINS 23–38 of preamplifier 132. In a preferred embodiment of the present invention, test probes 402 are place on contact pads 202, between head 118 and preamplifier 132. Test probes 402, however, may also be located on read element lead wires 303 and write element lead wires 304 or gull-wing leads 204. A low frequency signal is generated around a portion of read element 301 and inductive write element 302 once test probes 402 are placed in electrical contact at the desired location. The low frequency signal causes a test signal to be induced in read element 301 and inductive write element 302. A low frequency signal can be used because the location of test probes 402 eliminates the need for the induced signals to pass through preamplifier 132. Furthermore because a low frequency signal is used, undesirable stray currents are not induced in the head element electrical leads 303, 304 or gull wing lead wires 204. The present invention eliminates the need for dynamic testing.

FIG. 4 is illustrates test system 400 that relates to an embodiment of the present invention. HSA 200 is placed in tester 401. Tester 401 aligns and places test probes 402 in electrical contact with HSA's 200 head elements 301, 302 at some point in between the HSA'S 200 head 118 and preamplifier 132. Tester 401 may use optical or mechanic means to align test probes 402 to come into electrical contact with head elements 301, 302. Furthermore, tester 401 may use a mechanical positioning arm or some other apparatus to position test probes 402 in electrical contact with the head elements 301, 302. Test probes 402 are spaced, in an array, by pogo-pin board 403 such that each head element 301, 302 is individually electrically connected. In a preferred embodiment, a sufficient number of test probes 402 are present to contact each and every head electrical lead wire 303, 304 in HSA 200. Pogo-pin board 403 spaces test probes 402 to contact individual head electrical lead wires 303, 304, contact pads 202, gull wing leads 204 or any other point between a head 118 and preamplifier 132.

Tester 401 generates a changing magnetic field once test probes 402 are in place. The changing magnetic field induces test signals in each of the HSA's 200 head elements 301, 302. Tester 401 may use any method to generate the changing magnetic field; a coil may be used for example. The test signals from each head element 301, 302 are conducted through test probes 402 and into pogo-pin board 403.

The test signals pass through pogo-pin board 403 to the input of multiplexer 404. Multiplexer 404 may be any circuit or device that accepts multiple input signals, selects one or more, and produces the selected signal or signals at its output. Multiplexer 404 accepts the multiple test signals induced within the head elements 301, 302. Multiplexer 404 permits the test operator to select test signals from a specific head or heads 118 on HSA 200. The selected signals are passed from the output of multiplexer 404 to the input of op-amp 405, which amplifies the selected signals.

The amplified signals are then conducted to filter 406. Filter 406 is an electrical circuit that eliminates any unwanted interference signals that are present with the selected signal. Filter 406 can also reject unwanted signals within a specific frequency range.

The selected signals pass through high precision series resistor 407 once filter 406 eliminates the unwanted interference signals. A voltage drop develops across high precision series resistor 407 as the selected signals pass it. The resistance and precision of high precision series resistor 407 can be chosen according to the testing accuracy desired. The voltage across high precision series resistor 407 is measured using voltmeter 408. Another device capable of obtaining a voltage measurement can be used as an alternative to voltmeter 408. The voltage value obtained by voltmeter 408 is input into computer system 409. Computer system 409 can be any device capable of performing mathematical computations or signal analyzation.

Using Ohm's Law, computer system 409 calculates the current flowing through resistor 407. The current flowing through resistor 407 is equal to the current flowing through inductive write head element 302 because resistor 407 is in series with inductive write head element 302. Using the magnetic flux of the applied magnetic field, the number of turns of inductive head element 302, and the change in time, the voltage across inductive write head element 302 is also calculated by computer system 409. Computer system 409 can use Ohm's Law to determine the resistance of the inductive write head element 302 once the current and voltage of inductive write head element 302 is determined. The voltage and current present at resistor 407, the flux and frequency of the magnetic field applied by tester 401, the number of turns in inductive write element 302, and any other number of measured, calculated or known parameters, can used by computer system 409 to determine the selected inductive write head's 302 characteristics. Computer system 409 then outputs the results to output device 410. Output device 410 can be a display, printer, controller, monitor, or user interface among other things.

Figure 5:
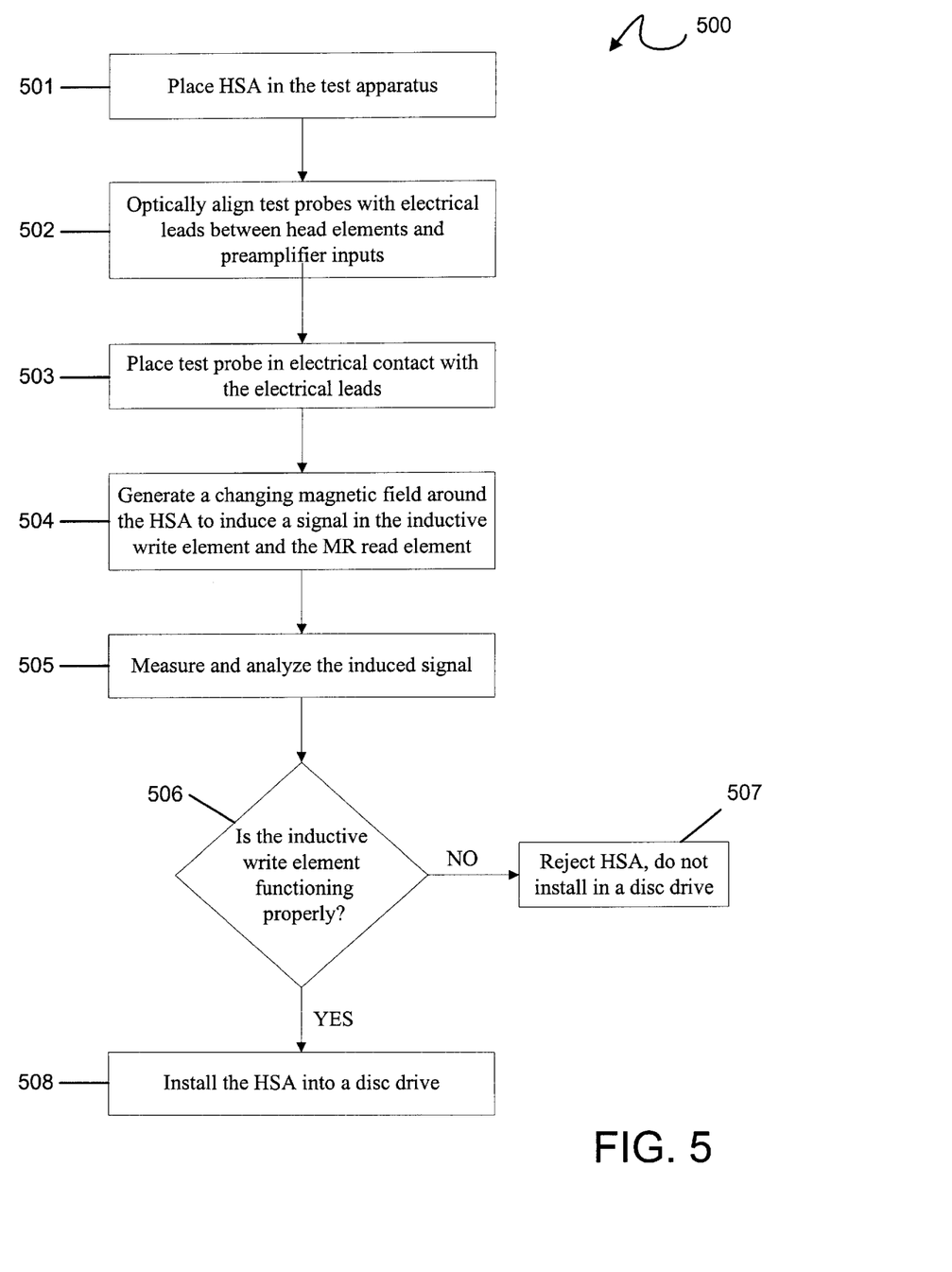
FIG. 5 is a flow diagram of the testing method in accordance with a preferred embodiment of the present invention.

FIG. 5 illustrates the operational flow process 500 that relates to an embodiment of the present invention for testing HSA 200. Operational flow process 500 begins by placing HSA 200 within testing apparatus 401 in operation 501. Once HSA 200 is in testing apparatus 401, optical alignment of the test probes 402 with the contact pads 202 of HSA 200 is completed in operation 502. It should be noted that the alignment system may utilize optical, mechanical, or any other alignment system to align the test probes 402 with the contact pads 202 of HSA 200.

Operational control shifts to operation 503 once operation 502 is complete. Operation 503 brings the test probes 402 and contact pads 202 into electrical contact with each other. Once an electrical connection is established by operation 503, control then shifts to operation 504, in which a changing magnetic field is generated around a portion of the head elements 301, 302 within HSA 200. The changing magnetic field induces an electric signal within each read and write element 301, 302. The induced signals are conducted through the head element leads 303, 304, to the contact pads 202, through the test probes 402, and into the test system. The induced signals are measured and analyzed to determine each head element's 301, 302 condition and characteristics in operation 505.

Operational control then passes to determination step 506. If the head elements 301, 302 are functioning properly determination, step 506 branches "YES" and control passes to operation 508. In operation 508, the properly functioning HSA 200 is installed into a disc drive (such as that show in FIG. 1). If one or more of the head elements 301, 302 is not functioning properly, determination step 506 branches "NO" and control passes to operation 507. In operation 507, the improperly functioning HSA 200 is rejected and is not installed into a disc drive.

It will be clear that the present invention is well adapted to attain the ends and advantages mentioned as well as those inherent therein. While a presently preferred embodiment has been described for purposes of this disclosure, various changes and modifications may be made which are well within the scope of the present invention. For example in another embodiment of the present invention, test probes 402 are placed on gull-wing leads 204 of preamplifier 132, between preamplifier 132 and contact pads 202. Each gull-wing lead 204, as in the previous embodiment, will have a corresponding test probe 402 in contact with it.

In yet another embodiment of the present invention, test probes 402 are placed on head element electrical leads 303, 304 between head 118 and contact pads 202. Each head element electrical lead 303, 304, as in the previous embodiments, will have a corresponding test probe 402 in contact with it.

In summary, the present invention may be viewed as method (as shown by operational flow process 500) of testing an inductive write element (such as 302) in a magnetic media read/write head (such as 118). The inductive write element (such as 302) has a predetermined number of coil turns and is electrically connected to a preamplifier (such as 132) via electrical leads (such as those shown in FIGS. 2 and 3). The method includes placing test probes (such as 402) of a test system (such as the test system shown in FIG. 4) in electrical contact with the inductive write element (such as 302) between the read/write head (such as 118) and the preamplifier (such as 132). The method further includes generating a changing magnetic field around a portion of the inductive write element (such as 302) inducing an electrical signal (the electrical signal having a current) to flow through the inductive write element (such as 302), through the test probes (such as 402), and into the test system (such as the test system shown in FIG. 4). The current of the electrical signal flowing into the test system (such as the test system shown in FIG. 4) is measured and the resistance of the inductive write element (such as 302) is calculated from the measured current, number of turns, and the predetermined changing magnetic field.

The method can be used on a HSA (such as 200) wherein the inductive write element electrical leads (such as 304) terminate at a bonding pad (such as 202), the bonding pads (such as 202) further being electrically connected to inputs of the preamplifier (such as 132) via preamplifier gull wing leads (such as 204). Furthermore, the method can be implemented by placing the test probes (such as 402) into electrical contact with the inductive write element (such as 302) at any point between the head (such as 118) and the preamplifier (such as 132). The test probes (such as 402) can by optically aligned with the electrical conductors between the head (such as 118) and the preamplifier (such as 132). The method can be implemented wherein numerous inductive write elements (such as 302) are simultaneously placed in electrical contact with numerous test probes (such as 402) and tested and wherein the read elements (such as 301) of a magnetic media read/write head (such as 118) are simultaneously tested with the inductive write element (such as 302), each read element (such as 301) having electrical leads (such as 303) connected to the preamplifier (such as 132). The method can be implemented wherein the inductive write elements (such as 302) are contained in a head stack assembly (such as 200). Finally, the method can be implemented wherein the generated changing magnetic field is of a sufficiently low frequency so as not to induce undesirable currents in the electrical leads (such as those shown in FIGS. 2 and 3) connecting the inductive write head element (such as 302) to the preamplifier (such as 132).

Alternatively, the present invention may be viewed as an apparatus for testing an inductive write element (such as 302) in a magnetic media read/write head (such as 118). The inductive write element (such as 302) has electrical leads (such as 304) connected to a preamplifier (such as 132). The apparatus has a test probe (such as 402), and an alignment mechanism to align the test probe (such as 402) with the electrical leads (such as 304) between the inductive write element (such as 302) and the preamplifier (such as 132). The apparatus also has a positioner arm to place the test probe (such as 402) in electrical contact with the inductive write element (such as 302) between the read/write head (such as 118) and the preamplifier (such as 132), an alternating magnetic field generator to induce an electrical signal in the inductive write element (such as 302), and a tester (such as the tester shown in FIG. 4) connected to the test probe (such as 402) operable to analyze the induced electrical signal.

The apparatus can simultaneously test numerous inductive write elements (such as 302), such as where the inductive write elements (such as 302) are assembled in a head stack assembly (such as 200). Furthermore, the apparatus has a sufficient number of test probes (such as 402) to simultaneously test numerous inductive write elements (such as 302). The apparatus may use a magnetic coil to induce an electrical signal in the inductive write element (such as 302). Additionally, the tester (such as the tester shown in FIG. 4) of the apparatus can determine the current flowing through, the voltage across, and the resistance of the inductive write element (such as 302). Finally, the apparatus can simultaneously test a read element (such as 301) of a magnetic media read/write head (such as 118) with the inductive write element (such as 302), the read element (such as 301) having electrical leads (such as 303) connected to the preamplifier (such as 132).

Numerous other changes may be made which will readily suggest themselves to those skilled in the art and which are encompassed in the spirit of the invention disclosed and as defined in the appended claims.

What is claimed is:

1. A method of testing an inductive write element in a magnetic media read/write head, the inductive write element having electrical leads connected to a preamplifier and the inductive write element having a predetermined number of coil turns, the method comprising steps of:

a) placing test probes of a test system in electrical contact with the inductive write element between the read/write head and the preamplifier;

b) generating a changing magnetic field around a portion of the inductive write element inducing an electrical signal to flow through the inductive write element, through the test probes, and into the test system, the electrical signal having a current;

c) measuring the current flowing into the test system;

d) calculating a resistance of the inductive write element from the measured current, the predetermined number of coil turns, and the changing magnetic field.

2. The method of claim 1, wherein the test probes in placing step (a) are placed into electrical contact with the inductive write element electrical leads at a bonding pad, the bonding pad connecting the inductive write element electrical leads and to the preamplifier.

3. The method of claim 1, wherein the test probes in placing step (a) are placed into electrical contact with the inductive write element at any point between the read/write head and the preamplifier.

4. The method of claim 1 wherein placing step (a) further comprises, optically aligning the test probes with an electrical conductor between the head element and the preamplifier.

5. The method of claim 1 wherein, a plurality of test probes in electrical contact with a plurality of inductive write elements are simultaneously tested.

6. The method of claim 5, wherein the inductive write elements are contained in a head stack assembly.

7. The method of claim 1, wherein a read element of the magnetic media read/write head is simultaneously tested with the inductive write element, the read element having electrical leads connected to the preamplifier.

8. The method of claim 1, wherein the changing magnetic field of generating step (b) is of a sufficiently low frequency so as not to induce an undesirable current in the electrical leads connecting the inductive write head element to the preamplifier.

9. An apparatus for testing an inductive write element in a magnetic media read/write head fastened to a distal end of an actuator arm, the inductive write element having electrical leads connected to a preamplifier mounted to the actuator arm, comprising:

a) a test probe;

b) an alignment mechanism to align the test probe with the electrical leads on the actuator arm connected between the inductive write element and the preamplifier;

c) a positioner arm to place the test probe in electrical contact with the inductive write element via the electrical leads between the read/write head and the preamplifier;

d) an alternating magnetic field generator to induce an electrical signal in the inductive write element; and e) a tester connected to the test probe operable to analyze the induced electrical signal.

10. The apparatus of claim 9, wherein a plurality of inductive write elements are tested simultaneously.

11. The apparatus of claim 10, wherein the inductive write elements are assembled in a head stack assembly.

12. The apparatus of claim 9, further comprising multiple test probes to simultaneously test a plurality of inductive write elements.

13. The apparatus of claim 9, wherein a magnetic coil is used to induce an electrical signal in the inductive write element.

14. The apparatus of claim 9, wherein the tester can determine a current flowing through, a voltage across, and a resistance of the inductive write element.

15. The apparatus of claim 9, wherein a read element of the magnetic media read/write head is simultaneously tested with the inductive write element, the read element having electrical leads connected to the preamplifier.

* * * * *